United States Patent
Birkhoff

(10) Patent No.: US 9,221,736 B2
(45) Date of Patent: Dec. 29, 2015

(54) PROCESS FOR PRODUCING PHENOL

(71) Applicant: BADGER LICENSING LLC, Boston, MA (US)

(72) Inventor: Ronald Birkhoff, Houston, TX (US)

(73) Assignee: BADGER LICENSING LLC, Boston, MA (US)

( * ) Notice: Subject to any disclaimer, the term of this patent is extended or adjusted under 35 U.S.C. 154(b) by 0 days.

(21) Appl. No.: 14/414,341

(22) PCT Filed: Jun. 17, 2013

(86) PCT No.: PCT/US2013/046056
§ 371 (c)(1),
(2) Date: Jan. 12, 2015

(87) PCT Pub. No.: WO2014/011359
PCT Pub. Date: Jan. 16, 2014

(65) Prior Publication Data
US 2015/0148568 A1    May 28, 2015

Related U.S. Application Data

(60) Provisional application No. 61/671,283, filed on Jul. 13, 2012.

(51) Int. Cl.
| | |
|---|---|
| *C07C 37/08* | (2006.01) |
| *C07C 2/66* | (2006.01) |
| *C07C 29/145* | (2006.01) |
| *C07C 2/86* | (2006.01) |
| *C07C 407/00* | (2006.01) |
| *C07C 37/68* | (2006.01) |
| *C07C 45/53* | (2006.01) |

(52) U.S. Cl.
CPC . *C07C 37/08* (2013.01); *C07C 2/66* (2013.01); *C07C 2/864* (2013.01); *C07C 29/145* (2013.01); *C07C 37/68* (2013.01); *C07C 45/53* (2013.01); *C07C 407/00* (2013.01); *C07C 2529/08* (2013.01); *C07C 2529/18* (2013.01); *C07C 2529/40* (2013.01); *C07C 2529/65* (2013.01); *C07C 2529/70* (2013.01)

(58) Field of Classification Search
None
See application file for complete search history.

(56) References Cited

U.S. PATENT DOCUMENTS

| | | | |
|---|---|---|---|
| 5,015,786 A | 5/1991 | Araki et al. | |
| 6,512,153 B1 * | 1/2003 | Cappellazzo et al. | 585/467 |
| 2010/0222609 A1 | 9/2010 | Dakka et al. | |
| 2011/0218366 A1 * | 9/2011 | Lorenzoni et al. | 568/798 |
| 2013/0172624 A1 | 7/2013 | Pecupero et al. | |

OTHER PUBLICATIONS

International Search Report and Written Opinion issued in the corresponding PCT/US2013/046056 on Aug. 13, 2013.

* cited by examiner

*Primary Examiner* — Brian J Davis
(74) *Attorney, Agent, or Firm* — Roberts Mlotkowski Safran & Cole, P.C.

(57) ABSTRACT

In a process for producing phenol, benzene is contacted with a C3 alkylating agent comprising isopropanol under alkylation conditions such that at least part of the isopropanol reacts with the benzene to produce cumene. At least part of the resultant cumene is then oxidized in the presence of an oxidizing gas to produce an oxidation effluent comprising cumene hydroperoxide, unreacted cumene and a spent oxidizing gas. The unreacted cumene is separated from the oxidation effluent and is treated to remove nitrogenous impurities therefrom and produce a purified cumene stream, which is recycled to the oxidization step. At least part of the cumene hydroperoxide from the oxidation effluent is cleaved to produce a cleavage effluent comprising phenol and acetone. The phenol is recovered phenol from the cleavage effluent, whereas at least part of the acetone from the cleavage effluent is hydrogenated to produce isopropanol for recycle to the alkylation step.

18 Claims, No Drawings

PROCESS FOR PRODUCING PHENOL

CROSS-REFERENCE TO RELATED APPLICATIONS

The present application is a U.S. National Phase of PCT/US2013/046056 filed on Jun. 17, 2013 claiming priority to U.S. provisional application No. 61/671,283 filed Jul. 13, 2012. The disclosure of the PCT Application is hereby incorporated by reference into the present Application.

FIELD

This invention relates to a process for producing phenol.

BACKGROUND

Phenol is an important product in the chemical industry with utility in, for example, the production of phenolic resins, ε-caprolactam, adipic acid, plasticizers and particularly Bisphenol A. The demand for phenol for the manufacture of Bisphenol-A and subsequently polycarbonates is accelerating, owing to the broadening applications of polycarbonates in the electronic, healthcare, and automobile industries.

Currently, the most common route for the production of phenol is the Hock process via cumene. This is normally a three-step process involving alkylation of benzene with propylene to produce cumene, followed by oxidation of the cumene to the corresponding hydroperoxide and then cleavage of the hydroperoxide to produce equimolar amounts of phenol and acetone.

The rapid growth of cumene, phenol and Bisphenol-A production, however, has caused some concerns related to the imbalance of the acetone byproduct produced from the phenol plant. Thus, acetone and phenol are produced at an approximately 1:1 molar ratio from cumene, but are used at an approximately 1:2 molar ratio in the downstream Bisphenol-A production process. The excess acetone that is not used in the production of Bisphenol-A has caused some concern from phenol producers in that it may create a supply-demand imbalance and disrupt the economics of the phenol production business. In addition, the cost of propylene is likely to increase, due to a developing shortage of propylene. Thus, a process that produces cumene, with less or no propylene as a feed, may be an attractive alternative route to the production of phenol.

Numerous research efforts have been directed at solving the acetone imbalance and propylene supply issues described above by recycling the excess acetone produced in the phenol plant to produce cumene. For example, U.S. Pat. No. 5,015,786 teaches a process for preparing phenol, comprising the steps of: (a) alkylating benzene with isopropanol using a zeolite catalyst under liquid phase conditions to synthesize cumene, (b) oxidizing the cumene from step (a) with molecular oxygen into cumene hydroperoxide, (c) subjecting cumene hydroperoxide to acid cleavage to synthesize phenol and acetone, and (d) hydrogenating the acetone from step (c) with hydrogen gas under liquid phase conditions into isopropanol which is recycled to step (a).

One problem in making cumene from isopropanol produced from the excess acetone from a phenol plant is that the acetone tends to contain significant quantities of nitrogen impurities which carry over into the isopropanol intermediate product. Such impurities act as poisons to the zeolite catalyst employed in the downstream alkylation step and so must be removed or reduced to very low levels. However, attempts to remove these impurities from the acetone and isopropanol feeds with conventional solid acid adsorbents have proved to be only marginally effective due to the molecular polarity of the acetone and isopropanol, which competes with the adsorption of the polar nitrogen compounds. Also, the high water solubility of acetone and isopropanol eliminates the use of water washing, which is otherwise commonly employed to remove nitrogen compounds from hydrocarbon streams.

In accordance with the present invention, it has now been found that one important contributor to the nitrogen impurities in the acetone intermediate is the caustic washing steps that are conventionally used to prevent build-up of organic acids in the phenol plant, for example during the cumene oxidation and phenol recovery stages. In particular, it has been found that nitrogen compounds employed in the phenol plant as corrosion inhibitors are transferred into the organic cumene phase during caustic washing of various cumene recycle streams. Transfer of these nitrogen compounds into the cumene recycle streams to the oxidation step results in formation of nitrogen impurities in the acetone product. However, cumene, unlike acetone and isopropanol, is susceptible to purification by conventional solid acid treatment and water washing. Thus the present invention seeks to avoid the problem of purification of the downstream acetone and isopropanol streams, by effecting nitrogen removal from the cumene recycle streams upstream in the phenol plant.

SUMMARY

In one aspect, the invention resides in a process for producing phenol, the process comprising:
   (a) contacting benzene with a $C_3$ alkylating agent comprising isopropanol, and optionally propylene, under alkylation conditions such that at least part of said isopropanol and benzene react to produce cumene;
   (b) oxidizing at least part of the cumene produced in (a) in the presence of an oxidizing gas to produce an oxidation effluent comprising cumene hydroperoxide and unreacted cumene and a spent oxidizing gas;
   (c) treating at least part of the unreacted cumene from the oxidation effluent to remove nitrogenous impurities therefrom and produce a purified cumene stream;
   (d) recycling the purified cumene stream to the oxidizing (b);
   (e) cleaving at least part of the cumene hydroperoxide from the oxidation effluent to produce a cleavage effluent comprising phenol and acetone;
   (f) recovering phenol from the cleavage effluent;
   (g) hydrogenating at least part of the acetone from the cleavage effluent to produce isopropanol; and
   (h) recycling at least part of the isopropanol from (g) to the contacting (a).

Generally, said treating (c) includes passing at least part of the unreacted cumene through a solid adsorbent, such as a molecular sieve or an acidic clay, and/or washing at least part of the unreacted cumene with an acidic aqueous solution.

In one embodiment, the process further comprises:
   (i) vaporizing cumene in said oxidation effluent to separate the unreacted cumene from the oxidation effluent and produce a concentrated cumene hydroperoxide stream;
   (j) feeding the concentrated cumene hydroperoxide stream to the cleaving (e); and
   (k) washing the cumene separated in (i) with a caustic solution and feeding the washed cumene to the treating (c).

In a further embodiment, the process further comprises:
   (l) recovering unreacted cumene from said spent oxidizing gas; and (m) washing the cumene recovered in (l) with a caustic solution and feeding the washed cumene to the treating (c).

Generally, the recovering (f) comprises fractionating the cleavage effluent to produce an acetone-containing stream, a phenol containing stream and a further stream containing unreacted cumene. The unreacted cumene in said further stream is then washed with a caustic solution and fed to the treating (c).

Conveniently, the contacting (a) takes place in the presence of hydrogen and a molecular sieve alkylation catalyst. The alkylation conditions typically comprise a temperature of 20° C. to 350° C., a pressure of 100 kPa to 20,000 kPa, and a molar ratio of benzene to $C_3$ alkylating agent fed to the alkylation zone 0.1:1 to 100:1.

DETAILED DESCRIPTION

A process is described for producing phenol from benzene. The process uses a modified version of the Hock process via cumene, in which the need for a propylene feedstock is obviated or minimized. The process involves four major stages. In the first stage, the benzene is alkylated by reaction with a $C_3$ alkylating agent, comprising isopropanol, over a zeolite catalyst. The cumene produced is then oxidized to the corresponding hydroperoxide in the second stage. The third stage involves cleavage of the cumene hydroperoxide to produce equimolar amounts of phenol and acetone, which are then typically supplied in a 1:2 molar ratio to Bisphenol-A production. In the fourth stage, the excess acetone from the third stage is hydrogenated to produce isopropanol, which is then recycled as part or all of the $C_3$ alkylating agent used in the first stage.

It has now been found that one of the problems associated with the above process is that the acetone fed to the hydrogenation stage normally contains reactive nitrogenous impurities (up to 10 ppm by weight). These impurities carry forward into the isopropanol and, unless removed, result in rapid poisoning and deactivation of the zeolite catalyst employed in the alkylation stage. The impurities have been traced to amine-based corrosion inhibitors that are added to reduce corrosion in condensate systems from organic acids generated as by-products of the oxidation and cleavage stages of the process. These amines are transferred into the organic phase during caustic washing of cumene recycle streams and result in the formation of nitrogen impurities in the acetone product. To minimize this problem, the unreacted cumene recovered in present process is treated to remove nitrogenous impurities before being recycled to oxidation stage. In this way, the reactive nitrogen levels in the isopropanol product of the hydrogenation reaction can be reduced.

Benzene Alkylation to Produce Cumene

In the first stage of the present process, benzene is alkylated with a $C_3$ alkylating agent comprising isopropanol, optionally together with added propylene, in the presence of a zeolite alkylation catalyst under conditions such that at least part of the reaction mixture is maintained in the liquid phase during the process. Typical conditions include a temperature of about 20° C. to about 350° C., for example about 60° C. to about 300° C., a pressure of about 100 kPa to about 20,000 kPa, for example about 500 kPa to about 10,000 kPa, and a molar ratio of benzene to the $C_3$ alkylating agent of about 0.1:1 to about 100:1, such as about 1:1 to about 10:1. Generally, the alkylation is conducted in the presence hydrogen, either added directly to the alkylation feed or present in the reactor effluent recycled from the fourth hydrogenation stage described below. Thus, it is found that hydrogen assists in removing the water coproduced with cumene in the alkylation step from the liquid phase reaction medium, thereby reducing the contact between the catalyst and the water and hence any tendency for the water to deactivate the catalyst. For some catalysts, the presence of hydrogen during the alkylation stage also reduces the deactivation caused by coke formation on the catalyst. Excessive hydrogen should, however, be avoided since it can lead to undesirable loss of benzene to cyclohexane. Conveniently, the molar ratio of hydrogen to isopropanol in said second reaction zone is about 0:1 to about 100:1, such as about 0:1 to about 10:1.

The catalyst employed in the alkylation step may comprise at least one medium pore molecular sieve having a Constraint Index of 2-12 (as defined in U.S. Pat. No. 4,016,218). Suitable medium pore molecular sieves include ZSM-5, ZSM-11, ZSM-12, ZSM-22, ZSM-23, ZSM-35, and ZSM-48. ZSM-5 is described in detail in U.S. Pat. Nos. 3,702,886 and Re. 29,948. ZSM-11 is described in detail in U.S. Pat. No. 3,709,979. ZSM-12 is described in U.S. Pat. No. 3,832,449. ZSM-22 is described in U.S. Pat. No. 4,556,477. ZSM-23 is described in U.S. Pat. No. 4,076,842. ZSM-35 is described in U.S. Pat. No. 4,016,245. ZSM-48 is more particularly described in U.S. Pat. No. 4,234,231.

Alternatively, the alkylation catalyst may comprise one or more large pore molecular sieves having a Constraint Index less than 2. Suitable large pore molecular sieves include zeolite beta, zeolite Y, Ultrastable Y (USY), Dealuminized Y (DealY), mordenite, ZSM-3, ZSM-4, ZSM-18, and ZSM-20. Zeolite ZSM-14 is described in U.S. Pat. No. 3,923,636. Zeolite ZSM-20 is described in U.S. Pat. No. 3,972,983. Zeolite Beta is described in U.S. Pat. Nos. 3,308,069, and Re. No. 28,341. Low sodium Ultrastable Y molecular sieve (USY) is described in U.S. Pat. Nos. 3,293,192 and 3,449,070. Dealuminized Y zeolite (DealY) may be prepared by the method found in U.S. Pat. No. 3,442,795. Zeolite UHP-Y is described in U.S. Pat. No. 4,401,556. Mordenite is a naturally occurring material but is also available in synthetic forms, such as TEA-mordenite (i.e., synthetic mordenite prepared from a reaction mixture comprising a tetraethylammonium directing agent). TEA-mordenite is disclosed in U.S. Pat. Nos. 3,766,093 and 3,894,104.

Preferably, however, the alkylation catalyst comprises at least one molecular sieve of the MCM-22 family. As used herein, the term "molecular sieve of the MCM-22 family" (or "material of the MCM-22 family" or "MCM-22 family material" or "MCM-22 family zeolite") includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of the MCM-22 family include those molecular sieves having an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques using the K-alpha doublet of copper as incident radiation and a diffractometer equipped with a scintillation counter and associated computer as the collection system.

Molecular sieves of the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), and mixtures thereof. Related zeolite UZM-8 is also suitable for use as the present alkylation catalyst.

The above molecular sieves may be used as the alkylation catalyst without any binder or matrix, i.e., in so-called self-bound form. Alternatively, the molecular sieve may be composited with another material which is resistant to the temperatures and other conditions employed in the alkylation reaction. Such materials include active and inactive materials and synthetic or naturally occurring zeolites as well as inorganic materials such as clays and/or oxides such as alumina, silica, silica-alumina, zirconia, titania, magnesia or mixtures of these and other oxides. The latter may be either naturally occurring or in the form of gelatinous precipitates or gels including mixtures of silica and metal oxides. Clays may also be included with the oxide type binders to modify the mechanical properties of the catalyst or to assist in its manufacture. Use of a material in conjunction with the molecular sieve, i.e., combined therewith or present during its synthesis, which itself is catalytically active may change the conversion and/or selectivity of the catalyst. Inactive materials suitably serve as diluents to control the amount of conversion so that products may be obtained economically and orderly without employing other means for controlling the rate of reaction. These materials may be incorporated into naturally occurring clays, e.g., bentonite and kaolin, to improve the crush strength of the catalyst under commercial operating conditions and function as binders or matrices for the catalyst. The relative proportions of molecular sieve and inorganic oxide matrix vary widely, with the sieve content ranging from about 1 to about 90 percent by weight and more usually, particularly, when the composite is prepared in the form of beads, in the range of about 2 to about 80 weight percent of the composite.

The alkylation step may be carried out batchwise or on a continuous basis. Moreover, the reaction may be carried out in a fixed or moving bed reactor. Fixed bed operation is, however, preferred, typically with the alkylation reaction zone comprising one or a plurality of series-connected beds of alkylation catalysts.

The alkylation step is generally operated so as to achieve substantially complete conversion of the $C_3$ alkylating agent (isopropanol plus any added propylene) and hence the effluent from the alkylation reactor is composed mainly of cumene, coproduced water, unreacted benzene, and other reaction products. Hydrogen will also be present in the effluent if it is present in the feed. Part of the effluent is typically recycled to the alkylation zone in order to control the reaction temperature. It is, however, important to avoid build-up of water in the alkylation reactor and hence the alkylation effluent is dewatered before the effluent is recycled. If hydrogen is present in the effluent, this is typically achieved by passing the effluent into a vapor/liquid separator to divide the effluent into a hydrogen-rich vapor stream and a hydrogen-depleted liquid stream. The hydrogen-rich vapor stream can then be recycled to the alkylation reactor, generally after being compressed and cooled to separate any entrained water and aromatics. The hydrogen-depleted liquid stream is separated into a water-rich aqueous stream and a water-depleted aromatic stream comprising cumene, unreacted benzene, and other reaction products. If hydrogen is not present in the effluent, the effluent stream can be cooled, separated into a water-rich aqueous stream and a water-depleted aromatic stream comprising cumene, unreacted benzene, and other reaction products.

After removal of the water and, if necessary, the hydrogen, the alkylation reaction effluent is passed to a distillation column, where the cumene is recovered and the unreacted benzene is removed for recycle back to the alkylation reaction zone.

Cumene Oxidation

The cumene recovered from the alkylation reaction effluent is converted to cumene hydroperoxide by a liquid phase oxidation process which is preferably carried out in a plurality of reactors connected in series. The oxidation process is conducted in the presence of an oxygen-containing gas, generally air, at a temperature from 50 to 120° C. and a pressure of 0 to 1 MPaG (gauge pressure). The total residence time in the oxidation reactors is usually from 3 to 20 hours.

The oxidation reaction may be carried out with or without a catalyst. Where a catalyst is employed, suitable catalysts include basic materials, such as carbonate and hydroxide compounds of alkali metals, such as lithium, sodium and potassium, and alkaline earth metals such as calcium and magnesium. These compounds may be used in solid form or in aqueous solution. The amount of catalyst (metal basis) is usually not more than 10 g equivalent, preferably 0.1 to 6 g equivalent per 1 ton of cumene.

The product of the oxidation reaction comprises a gas phase composed of spent air containing entrained cumene and a liquid phase which generally comprises 20 to 50% by weight of cumene hydroperoxide and 50 to 80% by weight of unreacted cumene, together with various by-products mainly composed of dimethyl phenyl carbinol (DMPC).

The gas phase product from the oxidation stage is cooled and then passed through a series of adsorbent beds, normally comprising charcoal, where the entrained cumene is removed before the spent air is vented to atmosphere or flared. The cumene collected by the charcoal adsorbers is recovered by desorption with low-pressure steam followed by condensation of the steam and decanting of the organic and water phases. The organic phase is then fed to a cumene recycle system described in more detail below.

The liquid phase product from the oxidation stage is heated in one or more stages, typically under vacuum, to remove most of the unreacted cumene and concentrate the cumene hydroperoxide in the product to 75 to 85 wt % before the product is fed to the cleavage step. The cumene vapor removed from the liquid phase product is cooled and combined with other cumene recycle streams produced in the process, such as the cumene recovered from the spent air, before being sent to the cumene recycle system.

Cumene Hydroperoxide Cleavage

The concentrated cumene hydroperoxide from the oxidation stage is decomposed or cleaved in the presence of an acid catalyst, normally sulfuric acid, mainly to phenol and acetone, while most of the DMPC by-product is converted to α-methylstyrene (AMS). The cleavage reaction is typically carried out at a temperature of about 40° C. to about 60° C. and a pressure of about 0 kPa to about 500 kPa.

The acid catalyst added to the cleavage reactor may be neutralized to prevent yield loss due to side reactions and to protect against corrosion in the downstream fractionation section. This is typically achieved by injecting caustic into the cleavage reactor effluent before the effluent passes to the fractionation section.

After neutralization, the cleavage effluent is initially passed to an acetone recovery section comprising at least a crude acetone recovery column and a finished acetone recovery column. In the crude acetone recovery column, the effluent is separated into a crude phenol bottoms stream, which is fed to a phenol recovery section, and a crude acetone overhead stream. The overhead stream is then fed to the finished acetone recovery column, where unreacted cumene and water are removed as a bottoms stream and acetone product is recovered as an overhead stream. After removal of the water, the unreacted cumene is sent to the cumene recycle system.

The crude phenol stream removed in the acetone recovery section is fed to a phenol recovery section which again comprises a multi-column distillation section, where a mixed cumene/AMS stream is removed before the crude phenol undergoes various chemical treatments and fractionation before a finished phenol product is recovered.

The mixed cumene/AMS stream removed in the phenol recovery section is initially subjected to a caustic wash to remove any residual acid and is then passed to a hydrogenation reactor where the AMS undergoes mild hydrogenation in the presence of a platinum catalyst to produce cumene with high selectivity. The resultant cumene enriched product is then sent to the cumene recycle system.

Generally, the phenol and acetone recovered from the cleavage reaction effluent are used in a molar ratio of 2:1 to produce Bisphenol A, thereby resulting in a net surplus of acetone.

Acetone Hydrogenation

In the present process, the excess acetone from the cleavage stage is hydrogenated to produce isopropanol for recycle to alkylation stage. The acetone hydrogenation is effected by contacting the excess acetone with hydrogen in the presence of metal-containing catalyst. Generally the catalyst is Raney nickel, but other useful catalysts include nickel, copper-chromium, Raney nickel-copper, copper-zinc and platinum group metals, for example, platinum, palladium, ruthenium, rhodium, and similar metals on active carbon, aluminum and other carriers. The reaction temperature may range from 20° C. to about 350° C., but more generally is between about 40° C. and 250° C., such as between about 60° C. and 200° C. The hydrogenation may be carried out by either liquid, gas, or mixed gas-liquid phase reaction. The pressure may range from 100 kPa to 20,000 kPa, such as from about 500 to about 10,000 kPa. The hydrogen gas is generally present in a molar ratio relative to the acetone reactant of from 0.1:1 to 100:1, such as from 1:1 to 10:1.

The hydrogenation may be carried out in the presence or absence of a reaction medium. Examples of suitable media include alcohols such as methanol, ethanol, propanols and butanols. Also useful are glycols such as ethylene glycol, propylene glycol, diethylene glycol, and triethylene glycol; and ethers such as diisopropyl ether, dibutyl ether, ethylene glycol dimethyl ether, diglyme (diethylene glycol dimethyl ether) and triglyme. Aprotic polar solvents may also be used, for example, dimethylformamide, dimethylacetamide, acetonitrile, and dimethyl sulfoxide. Also useful are saturated hydrocarbons such as hexane, heptane, cyclopentane, and cyclohexane. Water can also be used as a solvent in the hydrogenation reaction.

The hydrogenation step may be carried out batchwise or on a continuous basis. Depending on the shape of a particular catalyst used, the reaction may be carried out in a fluidized bed using powder catalyst or a fixed bed using granular catalyst. Fixed bed operation is preferred in view of ease of separation of the catalyst from the reaction mixture and simplicity of the reaction system.

The hydrogenation reaction is exothermic and, to avoid excessive temperature rise, part of the reaction effluent, composed mainly of isopropanol, can be cooled and recycled to hydrogenation reactor inlet. In one embodiment, the weight ratio of liquid recycle to acetone feed is between about 1:1 and about 100:1.

In addition, part of the unreacted hydrogen in the hydrogenation reaction effluent can be recycled to the hydrogenation reactor inlet so as to reduce the level of hydrogen in the isopropanol-containing feed to the alkylation step.

Treatment of Cumene Recycle Streams

It will be seen from the preceding discussion, that the present process generates a series of cumene recycle streams. To ensure process economics, these recycle streams are returned to the cumene oxidation stage. However, the cumene recycle streams contain acidic impurities generated and/or added during the oxidation and cleavage steps and their ancillary separation and purification stages. These acidic impurities inhibit the cumene oxidation reaction, and therefore the cumene recycle streams are treated with an aqueous caustic solution, such as sodium hydroxide solution, before being returned to the cumene oxidation stage. The caustic wash solution is produced by diluting concentrated caustic with demineralized water and condensed steam from the process. However, these process water streams tend to contain relatively high levels (up to 10 ppm by weight) of dissolved nitrogen compounds, particularly amines added to resist corrosion in the upstream distillation equipment. These nitrogen compounds are readily transferred to the organic phase at the high pH (normally from about 8 to about 14) used in the caustic washing step. Once transferred, these impurities tend to remain in the organic phase and pass from the cumene to the acetone and then to the isopropanol employed in the alkylation stage. Thus, in the cumene recycle system of the present process, the caustic washing step is followed by treatment of the recycled cumene to remove nitrogenous impurities therefrom. The treatment is generally carried out by passing at least part of the recycle cumene through a solid adsorbent, such as a molecular sieve or an acidic clay. In this way the nitrogen content in the isopropanol fed from the hydrogenation step to the alkylation step reaction can be reduced to less than 0.03 ppm by weight.

The invention claimed is:

1. A process for producing phenol, the process comprising:
(a) contacting benzene with a $C_3$ alkylating agent comprising isopropanol, and optionally propylene, under alkylation conditions such that at least part of said isopropanol and benzene react to produce cumene;
(b) oxidizing at least part of the cumene produced in (a) in the presence of an oxidizing gas to produce an oxidation effluent comprising cumene hydroperoxide and unreacted cumene and a spent oxidizing gas;
(c) treating at least part of the unreacted cumene from the oxidation effluent to remove nitrogenous impurities therefrom and produce a purified cumene stream;
(d) recycling the purified cumene stream to the oxidizing (b);

(e) cleaving at least part of the cumene hydroperoxide from the oxidation effluent to produce a cleavage effluent comprising phenol and acetone;
(f) recovering phenol from the cleavage effluent;
(g) hydrogenating at least part of the acetone from the cleavage effluent to produce isopropanol; and
(h) recycling at least part of the isopropanol from (g) to the contacting (a).

2. The process of claim 1, wherein said treating (c) includes passing at least part of the unreacted cumene through a solid adsorbent.

3. The process of claim 2, wherein said solid adsorbent comprises a molecular sieve or an acidic clay.

4. The process of claim 1, wherein at least part of the unreacted cumene from (b) is washed with an acidic aqueous solution prior to said treating (c).

5. The process of claim 1 and further comprising:
(i) vaporizing cumene in said oxidation effluent to separate the unreacted cumene from the oxidation effluent and produce a concentrated cumene hydroperoxide stream;
(j) feeding the concentrated cumene hydroperoxide stream to the cleaving (e); and
(k) washing the cumene separated in (i) with a caustic solution and feeding the washed cumene to the treating (c).

6. The process of claim 1 and further comprising:
(l) recovering unreacted cumene from said spent oxidizing gas; and
(m) washing the cumene recovered in (l) with a caustic solution and feeding the washed cumene to the treating (c).

7. The process of claim 1, wherein said recovering (f) comprises fractionating said cleavage effluent to produce an acetone-containing stream, a phenol containing stream and a further stream containing unreacted cumene.

8. The process of claim 7, wherein the unreacted cumene in said further stream is washed with a caustic solution and then fed to the treating (c).

9. The process of claim 1, wherein said contacting (a) takes place in the presence of a molecular sieve alkylation catalyst.

10. The process of claim 9, wherein said alkylation catalyst comprises at least one zeolite catalyst selected from the group consisting of ZSM-3, ZSM-4, ZSM-5, ZSM-11, ZSM-12, ZSM-14, ZSM-18, ZSM-20, ZSM-22, ZSM-23, ZSM-35, ZSM-48, zeolite beta, zeolite Y, Ultrastable Y (USY), Deluminized Y (Deal Y), mordenite, MCM-22, PSH-3, SSZ-25, ERB-1, ITQ-1, ITQ-2, MCM-36, MCM-49, MCM-56, and UZM-8.

11. The process of claim 9, wherein said alkylation catalyst comprises at least one zeolite catalyst selected from the group consisting of MCM-22, PSH-3, SSZ-25, ERB-1, ITQ-1, ITQ-2, MCM-36, MCM-49, MCM-56, UZM-8, and mixtures thereof.

12. The process of claim 1, wherein said alkylation conditions comprise a temperature of 20° C. to 350° C., a pressure of 100 kPa to 20,000 kPa, and a molar ratio of benzene to $C_3$ alkylating agent fed to said alkylation zone of 0.1:1 to 100:1.

13. The process of claim 12, wherein the molar ratio of benzene to $C_3$ alkylating agent fed to said alkylation zone ranges from 0.3:1 to 10:1.

14. The process of claim 12, wherein the temperature ranges from 100 to 300° C.

15. The process of claim 1, wherein said $C_3$ alkylating agent comprises a mixture of isopropanol and propylene at molar ratio of isopropanol to propylene of about 0.01:1 to about 100:1.

16. The process of claim 12, wherein the molar ratio of benzene to $C_3$ alkylating agent fed to said alkylation zone ranges from 0.5:1 to 5:1.

17. The process of claim 12, wherein the molar ratio of benzene to $C_3$ alkylating agent fed to said alkylation zone ranges from 1:1 to 3:1.

18. The process of claim 12, wherein the temperature ranges from 150 to 280° C.

* * * * *